United States Patent [19]

Lintilhac et al.

[11] Patent Number: 5,452,236
[45] Date of Patent: Sep. 19, 1995

[54] INSTRUMENT FOR CONTROLLING THE APPLICATION OF MECHANICAL LOADS TO BIOLOGICAL AND BICOMPATIBLE TEST SUBJECTS

[75] Inventors: Phillip M. Lintilhac, Shelburne; Thompson B. Vesecky, Essex Junction, both of Vt.

[73] Assignee: John Chatillon & Sons, Inc., Greensboro, N.C.

[21] Appl. No.: 349,468

[22] Filed: Dec. 5, 1994

Related U.S. Application Data

[60] Continuation of Ser. No. 81,811, Jun. 23, 1993, abandoned, which is a division of Ser. No. 477,332, Feb. 8, 1990, abandoned.

[51] Int. Cl.[6] ............................................. G05D 15/01
[52] U.S. Cl. ...................................... 364/550; 73/763
[58] Field of Search ............... 364/506, 507, 508, 512, 364/514, 550, 551.01; 128/774; 73/1 B, 760, 763, 769, 788

[56] References Cited

U.S. PATENT DOCUMENTS

| | | |
|---|---|---|
| 2,154,280 | 4/1939 | Nadai et al. |
| 3,255,627 | 6/1966 | Doig et al. |
| 3,712,125 | 1/1973 | Meyer |
| 3,927,558 | 12/1975 | Philippe et al. |
| 4,096,741 | 6/1978 | Sternstein |
| 4,184,424 | 1/1980 | Yeager et al. |
| 4,235,114 | 11/1980 | Mohler |
| 4,448,079 | 5/1984 | Schumacher et al. |
| 4,480,480 | 11/1984 | Scott et al. ............... 364/512 X |
| 4,566,868 | 1/1986 | Menzies |
| 4,572,001 | 2/1986 | Saimoto et al. |
| 4,802,367 | 2/1989 | Petersen et al. |
| 4,866,991 | 9/1989 | Tse |
| 4,901,581 | 2/1990 | Fain et al. |
| 5,046,367 | 9/1991 | Iizuka |

FOREIGN PATENT DOCUMENTS

| | | |
|---|---|---|
| 2607929 | 6/1988 | France |
| 3719380C1 | 5/1988 | Germany |
| 60-161542 | 8/1985 | Japan |
| 62000135 | 1/1987 | Japan |
| 2163870 | 3/1976 | United Kingdom |
| 0913138 | 3/1982 | U.S.S.R. |

OTHER PUBLICATIONS

Wu & Jerina, "Computer-Aided Mechanical Testing of Composites," *Materials Research and Standards*, vol. 12, No. 2 (Feb. 1970).

Bunsell, Hearle & Hunter, "An Apparatus for Fatigue-Testing Fibres," *Journal of Physics E: Scientific Instruments*, vol. 4, No. 11 (Nov. 1971).

*Primary Examiner*—Ellis B. Ramirez
*Assistant Examiner*—Edward Pipala
*Attorney, Agent, or Firm*—Brumbaugh Graves Donohue & Raymond

[57] ABSTRACT

Apparatus and methods are disclosed facilitating the application of forces and measurement of dimensions of a test subject. In one arrangement the test subject is coupled to a forcing frame and controlled forces applied thereto. Force applied to the test subject is measured and controlled. A dimensional characteristic of the test subject, such as growth, is measured by a linear variable differential transformer. The growth measurement data can be used to control the force applied. The transducer module receives force and dimensional data from the forcing frame. The transducer module is a separate, microprocessor-based unit that communicates the test data to a controller unit that controls the application of force to the test subject and receives the test data from the transducer module for force control, storage, and/or communication to the user.

6 Claims, 4 Drawing Sheets

INSTRUMENT FOR CONTROLLING THE APPLICATION OF MECHANICAL LOADS TO BIOLOGICAL AND BICOMPATIBLE TEST SUBJECTS

The Government of the United States of America has rights in the invention directed to the microcomputer-based controller system (digital controller) and the system of displacement transducers for continuous growth measurement (incorporation of linear variable differential transformers) pursuant to Contract No. DE-AC02-ER80373 awarded by the U.S. Department of Energy.

This application is a continuation of application Ser. No. 08/081,811, filed on Jun. 23, 1993 now abandoned which application is in turn a divisional application of application Ser. No. 07/477,332, filed on Feb. 8, 1990.

BACKGROUND OF THE INVENTION

The present invention relates to a device for applying controlled mechanical forces to test specimens, particularly biological test specimens, such as living tissue growing in cultures and biocompatible materials intended for use in a biological environment, such as suture materials, materials for implants, etc. More particularly the invention relates to an arrangement for accurately manipulating a specimen, accurately measuring mechanical forces that it applies, and for accurately measuring the specimen's size and/or growth.

U.S. Pat. No. 4,456,683 (hereinafter "the '683 patent") to Lintilhac et al., is incorporated herein by reference. The '683 patent discloses a sterilizable device having a forcing frame with specimen interface members to contact and apply forces to a biological specimen. The interface members can be gradually and accurately adjusted toward and away from each other in order to provide a direct mechanical force to living tissue disposed between the members. The application of the mechanical forces to living tissue in the device disclosed in the '683 patent permits the study of effect of forces on living tissue, cell structure and cell division. For both biological compatible materials, it can simulate pressures of surrounding tissues existing in the specimen's natural environment.

SUMMARY OF THE INVENTION

The present invention provides versatile apparatus for readily coupling a biological test subject with a force generating device like that, for example of the '683 patent. In one preferred embodiment, the apparatus comprises a base and one or more sliders that engage the test subject. The base has at least one guideway, receiving the slider or sliders. Each guideway is an elongated slot in the base. The sides of the slot define parallel guide rails for engaging the sides of the sliders and for guiding the sliders. An upper portion of each slider rises above the guide rails for force imparting connection to the force generating device. The sliders can slide freely along the axis of the guideway. In one embodiment each slider has a working portion or tip shaped to engage the biological test subject at a region of relatively small surface area. The other end of the slider has a recess in the upper portion for receiving force transmitting members depending from the force generating device. The recess is a slot in the upper portion of the slider, generally transverse to the axis of movement of the slider along the guideway. The base and slotted sliders enable positioning a test subject at a location remote from the force generating device, outside of the sterile environment. With the depending force transmitting members appropriately positioned, the force generating device and the base and slider combination can be readily brought together inside an enclosure to be sterilized. Set up is greatly simplified.

In one configuration of the apparatus for coupling, two sliders are spaced axially along one guideway. The working portions are ends of the sliders facing each other so that the test subject can be connected between them. Force transmitting members secured to the force generating device are inserted into the recesses of the two sliders. The force generating device can then be operated to cause the sliders to apply compression or tension to the test subject as desired.

In a second configuration, one slider is received in a center guideway with its working portion extending to the location of the test subject. This first slider is operatively connected to the force generating device via a first force transmitting member at one side of the location of the test subject. Second and third sliders are received in second and third guideways, respectively, on opposite sides of the first guideway. The second and third sliders are generally on the opposite side of the test subject location from the first slider with their working portions extending to the location of the test subject. The second and third sliders are adapted to operatively connect to the force generating device via a second force transmitting member on the opposite side of the test subject location. This arrangement provides for three point bending of the test subject located in the test subject location and engaged by the working portions of the three sliders. The working portion for these three sliders are transverse slots that can be aligned to receive the test subject.

In another configuration, the base has two guideways with intersecting axes. Each guideway slidably receives a pair of sliders with working portions facing the intersection of the guideways. One of the two pairs of sliders provides means for locating the test subject for connection to the other pair of sliders. Alternatively, both pairs of sliders can engage the test subject in force exerting relation, whereby forces can be applied by the sliders along the intersecting axes of the guideways using first and second force generating devices.

In a further exemplary embodiment of the present invention the apparatus for coupling the test subject to the force generating device is an arrangement for stretching an elastic band support for the test subject. The apparatus for coupling the test subject to the force generating device comprises a pair of rods around which wrap the ends of the band. Each of a pair of elastic band retaining members is adapted to fit around one of the rods in a partially encircling relation to trap the test subject supporting band end between the rod and the retaining members. Each of the force transmitting members adapted for connection to the force generating device has curved appendages adapted to fit partially around the rod at spaced locations on opposite sides of the elastic band end retained on the rod. The test subject is affixed to the band by using a commercially available glue or in the case of cells or other biological test subjects, one can use a coating of a substance to which the specimen is known naturally to adhere. In this configuration, the displacement of the rods and band ends by the force transmitting members can cause substantially unidirectional stretching of the elastic band to stress the supported biological test subject in a selected direction.

The combination of the force generating device, such as that disclosed in the above-mentioned '683 patent, and means for coupling the test subject thereto, as just described, provides a test arrangement that is easily used and controlled. Additional features enhance that combination's ability to control and to measure sustained or variable forces, growth, compression or flexure. In a force frame like that of the mentioned patent, the force is generated by an electrically controlled pneumatically or hydraulically operated bellows extending between the force transmitting members that are received in the recesses of the sliders or other members engaging the test subject.

In accordance with the invention, connected to the force generating device is a transducer for electrically measuring the distance of movement of the force transmitting means. This provides monitoring of dimensional changes in a test subject. Alternatively, the use of a means for measuring distance permits use of the force applying device in an isometric (or other controlled dimension) mode wherein size is held constant (or is a controlled parameter) and force is measured. The preferred device for measuring the distance of movement (or size) is a linear variable differential transformer (LVDT) connected between movable members of the force generating means connected to the force transmitting members.

The force generating device is supported by a removable closure of a test container. The forcing means position within the container can be adjusted in order to bring the force transmitting means into cooperation with recesses in the sliders. The force producing means can effect changes in the spacing of depending force transmitting members. A positionally adjustable mechanical mount extending through the closure is used to align the forcing means horizontally and vertically with respect to the closure. This provides means for adjusting the position of the force transmitting members with respect to the sliders and base positioned in the test container, in order to bring the force transmitting members into the recesses of the sliders without opening the test container and contaminating the test environment.

The present invention combines into one instrument the ability very accurately to apply force to and measure the size of a test subject in a controlled environment. The force generating device, a force measuring arrangement (like the strain gauges of the '683 patent for example), and the transducer operatively connected to the force generating device for measuring the distance between or distance of movement of the pair of force transmitting members enable a greater degree of control over the environment of the test subject. The change in the distance between the pair of force transmitting members controlled by the forcing device is related to the change in the size, shape, bending or the like of the test subject. The strain gauge indication of force indicates the force being applied to the subject. These indications can be used as feedback to a controller. The size or force can be regularly, repeatedly varied a desired amount, or size or force can be maintained constant and the remaining indication can be monitored.

A controller for determining size and/or force applied to a specimen, for programming the application of forces or changes in dimension, and for displaying and recording resulting growth, compression, force generation and the like, includes a microprocessor in control of a stepper motor driving a pneumatic or hydraulic pump that precisely controls the bellows that positions the force transmitting members of the force generating device. Suitable interface circuitry of a transducer module converts analog measurements of the dimension-measuring transducer (LVDT) and bridge-connected strain gauges to suitable digital indications communicated to the controller. The controller communicates with the experimenter by display and keyboard, allowing the experimenter to program a regimen, or choose one previously retained in memory. Force and dimensional parameters can be selected. An interface enables communications from an analog function generator, for example to input a force waveform. Another interface is provided for communication with a printer, whereby results can be plotted or listed. Alternatively an interface provides an analog output to, say, a chart recorder to graph experiment output data. And a PC interface permits a personal computer to dictate the course of an experiment or to receive, store and/or mathematically deal with output data.

BRIEF DESCRIPTION OF THE DRAWINGS

The above and further advantages of the invention will be better understood with respect to the following detailed description of a preferred embodiment, taken in combination with the several figures of the associated drawings, in which.

DESCRIPTION OF THE PREFERRED EMBODIMENTS

Figure 1:
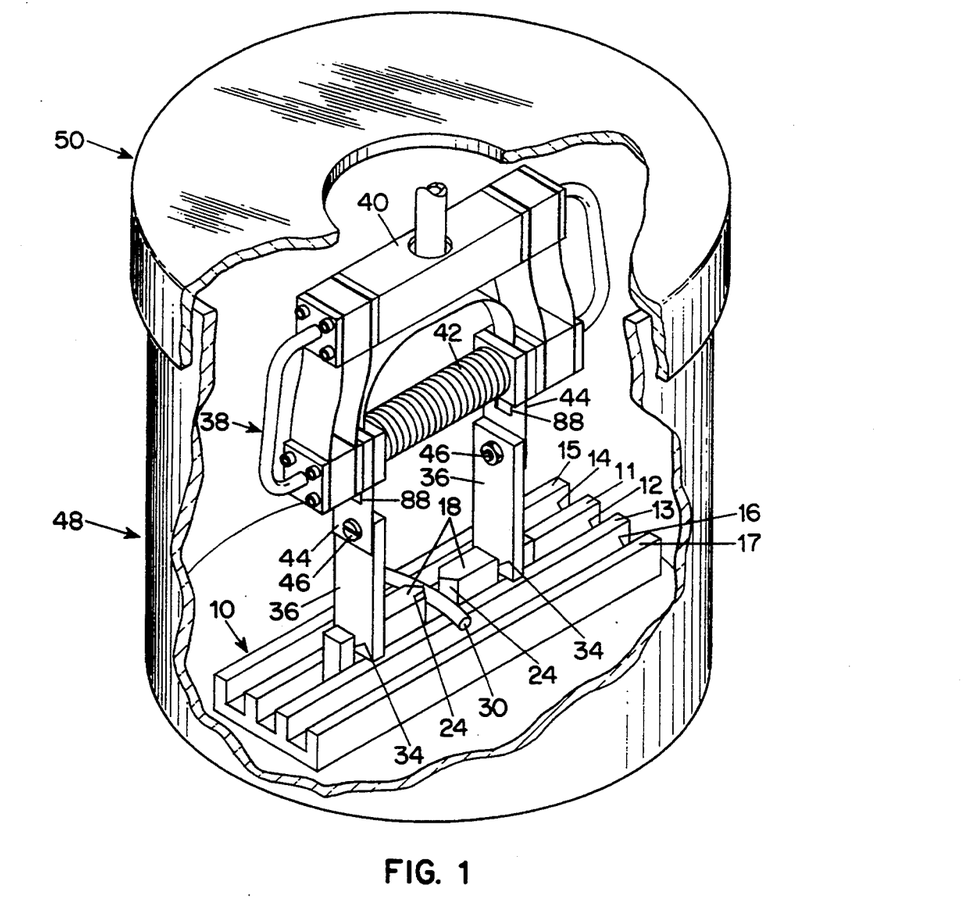
FIG. 1 is a perspective view of one embodiment of the invention and shows a force generating device, in combination with an apparatus for coupling a test subject to the device.

With reference to FIG. 1, a base 10 has a center guideway 12 and two adjacent guideways 14 and 16. The three guideways 12, 14 and 16 are elongated slots whose sides 11, 13, 15, and 17 define parallel guide rails in the base 10 for engaging the sides of at least one slider 18. In FIG. 1, two sliders 18 are spaced axially along and slidably received in the center guideway 12. Each slider 18 has a height greater than the depth of the center guideway 12. The top of each slider 18, then, rises slightly above the top of the guideway sides 11 and 13.

One end of each slider 18 is tapered, defining a working portion 24. The tapered end provides a relatively small surface area engaging a test subject 30, such as living tissue. The working portion of each slider 18 received in the center guideway 12 faces toward the center of the test subject location. If only compression of the test subject is contemplated nothing more may be needed to retain the test subject in place. If the subject is to be placed in tension, a commercial glue can be used to attach it to the slider working portions. The glue chosen can be sterilizable or nonsterilizable, depending on the requirements of the particular investigation.

Each slider 18 has a slot 34 in its top transverse to its axis of movement along guideway 12. Paddle-like force transmitting members 36 of a force generating device or forcing frame 38 are received in the slots 34. The force transmitting members 36 are thin, rigid, rectangular blocks. The lower portions of the force transmitting members 36 should fit snugly into the recesses 34, if no relative motion along the axis of the guideway 12 is to occur between the force transmitting members 36 and the sliders 18. The fit between the two components, however, should be such that the force transmitting members 36 can be easily moved into and out of the recesses 34 by lowering or lifting the forcing frame 38. As a result of this configuration, the assembly consisting of the base 10, slider 18 and the forcing frame 38 can easily be set up before an experiment as will be described.

The forcing frame 38 is described in detail in the '463 patent to Lintilhac et al. Basically, the forcing frame 38 has a header block 40 connected to an electrically controlled pneumatic or hydraulic bellows 42. Connected with either end of the bellows 42 is an instrumental shim 44 extending downward. For each instrumental shim 44, a nut and bolt 46 tightly secure the lower end of the shim 44 to the upper end of one of the force transmitting members 36. The shims 44 are constructed of material such as stainless steel to minimize blending of the shims while force across the bellows 42 is transmitted through the shims 44 to the force transmitting members 36. When the bellows 42 contracts, compression force is applied to the test subject 30 via the shims 44, the force transmitting members 36, and the sliders 18. Conversely, when the bellows 42 expands, tension is applied to the test subject 30.

Figure 1A:
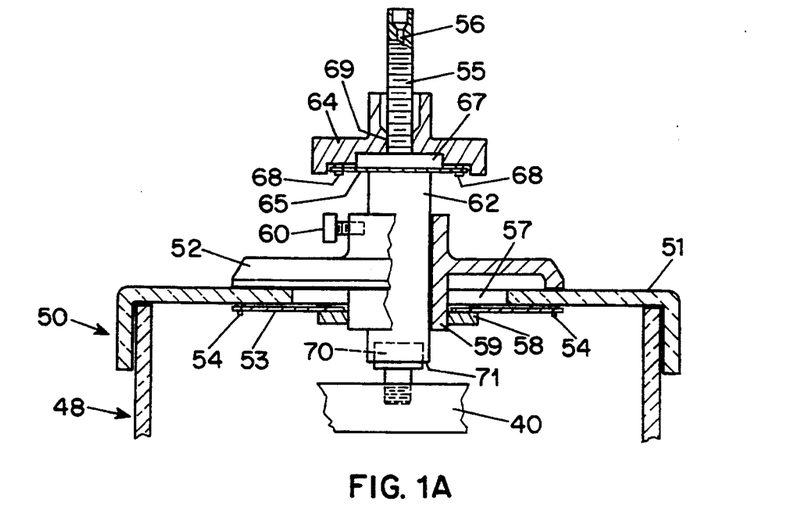
FIG. 1A is an enlarged fragmentary cross-sectional view of an adjustable support for the force generating device of FIG. 1 in cooperation with the lid of a test container.

The forcing frame 38 is supported by a removable lid 50 on a test container 48. Better seen in FIG. 1A, a positioner housing 52 and a thin disc-shaped spider 53 grip between them the top 51 of the lid 50. Six teflon headed screws 54 engage the underside of the lid top 51. A spider spring adjustment nut 58 threaded on to a downward extension 59 of the positioner housing 52 holds the spider 53 firmly to the under surface of the glass lid 50. A vertical positioner rod 55 extends through the positioner housing 52 and the spider 53 to header block 40 of the forcing frame 38 to support the forcing frame from above. The positioner rod 55 has a central axial opening 56 communicating with the header 40 interior to direct air or motive fluid to the header from a pump 239 in FIG. 7. The positioner housing 52 and the spider 53 are laterally movable with respect to the lid 50 by virtue of an enlarged opening 57 through the lid. The user can grip the housing 52 to move the whole frame frontward or backward, or side-to-side, or to rotate the frame. A coarse height adjustment screw 60 can be loosened to permit sliding of a barrel 62 up or down. The barrel 62 is held snug to a vertical adjustment wheel 64 by a thin wheel clamp 65 entrapping an enlarged head 67 of the barrel. Two screws 68 secure the clamp 65 and barrel head 67 to the underside of the wheel 64. With the screw 60 tightened, fine vertical adjustment is accomplished by turning the vertical adjustment wheel 64 which is threaded internally and in threaded engagement with a threaded portion of the rod 55 at 69. The rod 55 is slidable in the barrel 62 but is held against rotation by a noncircular opening through a tapered teflon bearing 70 screwed into the end or nosepiece 71 of the barrel and receiving a complementary noncircular, and unthreaded portion of the rod.

The combination of the base 10 with sliders 18 and the positionable forcing frame 38 mounting provisions affords easy set-up of a test or experiment. The test subject 30 is located between the sliders 18 (glued to them if necessary). The base 10 and sliders 18 are placed centrally on the bottom of the container 48. The lid 50 is placed on the container 48 and the force transmitting members 36 are aligned with the slots 34 in the sliders 18. The forcing frame 38 is lowered until the force-transmitting members 36 are received in the slots 34. If the spacing between the force transmitting members 36 needs adjustment, this can be effected using the force generating bellows 42 of the forcing frame 38 under control of the pump 239 of FIG. 7. The interior of the container 48, the frame 38 and the base 10 and sliders 18 can all be sterilized beforehand and the set-up as described can be effected in an incubator.

Figure 2:
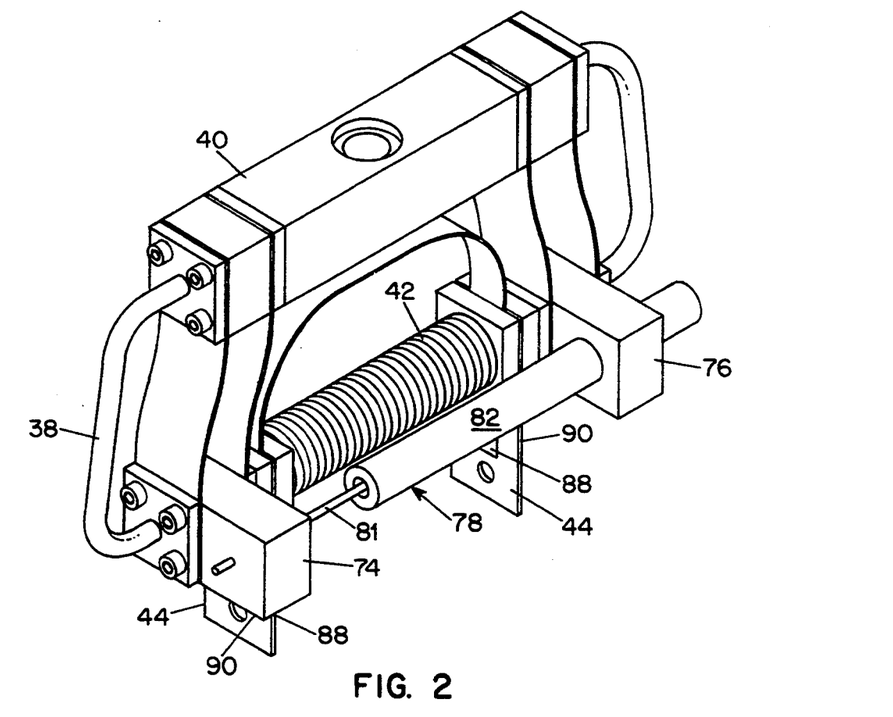
FIG. 2 is an enlarged perspective view of a force generating device like that of FIG. 1 and shows a distance measuring transducer thereon.

As shown in FIG. 2, for the purpose of providing an electrical indication of size or the change in size of a test subject, secured to either end of the bellows 42 and the header block 40 are stainless steel spacer blocks 74, 76 supporting an LVDT 78. The spacer blocks 74, 76 extend perpendicularly from the plane of the bellows 42 and header block 40 and are movable with the shims 44. The shims 44 and blocks 74 and 76 move apart as the test subject 30 grows or is stretched under the influence of the bellows 42. Conversely, as the engaged portion of the test subject 30 contracts or is compressed, the shims 44 and blocks 74 and 76 move closer together.

The LVDT 78 can be a commercially available product such as the 200LW model available from Schaevitz Engineering of Pennsauken, N.J. Secured to the block 74 is a movable core 81. Secured to the other movable spacer block 76 is the transducer's coil housing 82. The LVDT 78 chosen for this application has a chromium-coated stainless steel coil housing 82, a tapered layer-wound coil assembly inside the housing (not shown in FIG. 2), and the core 81, a movable, Teflon-coated nickel-iron core having one end inserted into one end of the coil housing. The movable core 81 can freely slide inside the coil in the housing 82. As the distance changes between the movable blocks 74, 76, relative movement of the core 81 and housed coils enable the appropriately energized LVDT 78 to produce an output electrical signal that varies with the relative position of the core and the coils. The LVDT 78 and an appropriate LVDT signal conditioner circuit such as the Signetics NE/SA/SE/5521 LVDT signal conditioner, provide, then, the means for a continuous size measurement of the dimension of test subject 30 in a direction parallel to the LVDT. The signal conditioner provides appropriate input excitation of the LVDT primary and appropriate demodulation of the output from the secondary.

As disclosed in the '683 patent, each instrumental shim 44 carries a strain gauge 88 (only one of which can be seen in FIG. 2) on the inside face of the instrumental shim, each carries a strain gauge 90 (hidden in FIG. 2) on the outside face of the instrumental shim 44. As described in the above referenced patent, the voltage drop across the strain gauges 88 and 90, preferably connected in a bridge configuration, provide continuous measurement of the force being applied to the test subject 30.

Figure 3:
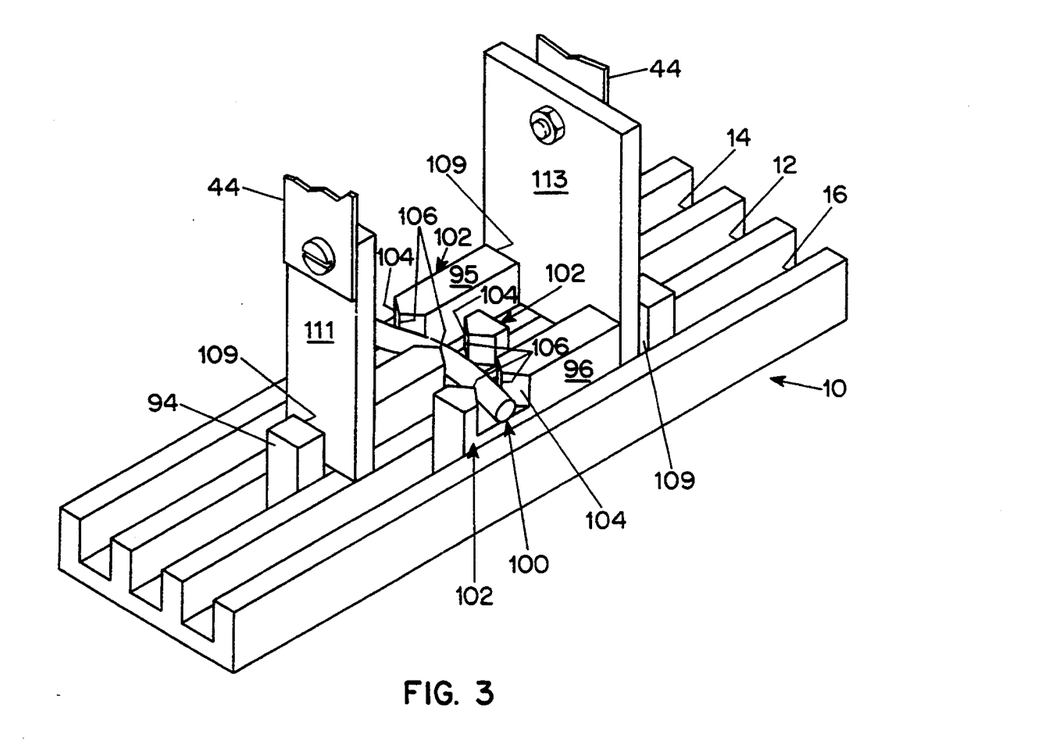
FIG. 3 is a fragmentary, enlarged perspective view of force transmitting parts of a force generating device like that of FIG. 1, and a coupling apparatus arranged to be used in three point bending.

FIG. 3 shows an alternate base and slider arrangement. Three sliders 94, 95 and 96 reside on the base 10 in the three guideways 12, 14, 16, respectively, and apply three point bending forces to a test subject 100. Each of the sliders 94, 95 and 96 has a working end 102, slotted at 104 to receive the test subject 100. Sides of the slots 104 are pointed at 106 to define a precise point of contact. Transverse slots 109, are formed in the farther ends of the sliders. The slots 109 are similar to slots 34 described with respect to FIG. 1. A first force transmitting member 111 is snugly received in the slot 109 of the slider 94. A wider force transmitting member 113 has edge portions received in the slots 109 of the sliders 95 and 96. The force transmitting members 111 and 113 are secured to the shims 44 of the forcing frame. It will be appreciated that forces applied to the test subject 100 by the forcing frame effect three point bending of the subject. The pointed sides 106 of the slots 104 enable the investigator to know exactly the distance between the force application points.

Figure 4:
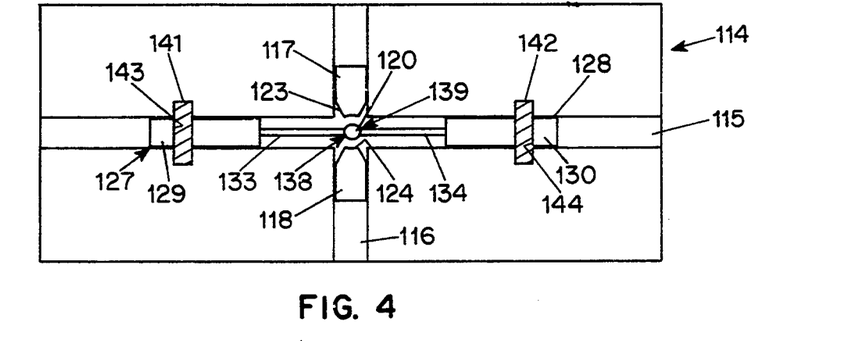
FIG. 4 is a top plan view, partially in section, of a coupling apparatus with intersecting guideways for sliders movable therein.
Figure 5:
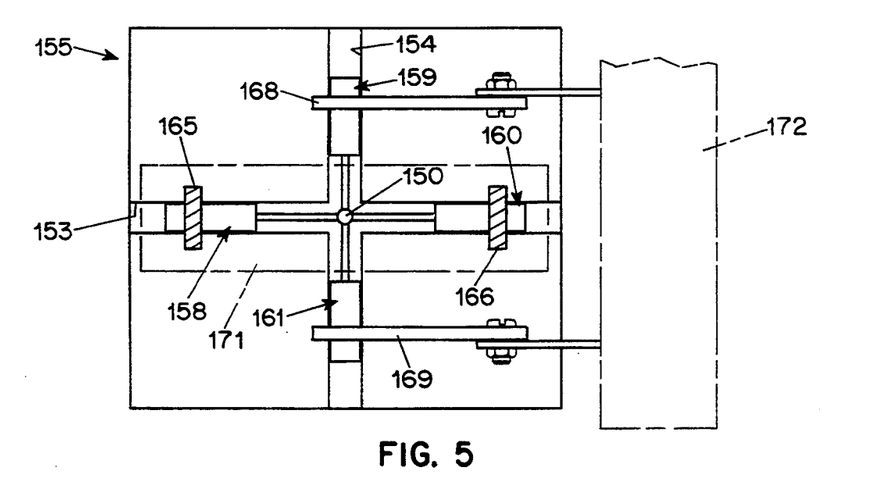
FIG. 5 is a top plan view, partially in section, of intersecting guideways each with sliders, for applying forces on orthogonal axes.

Two further configurations of base and sliders are illustrated in FIGS. 4 and 5. In FIG. 4, a rectangular base 114 has two perpendicular intersecting slots 115 and 116 formed in the upper surface thereof. Two sliders 117 and 118 reside in the slot 116 on opposite sides of a test subject 120. These are positioning sliders. They have working ends 123 and 124 that are shaped to assist holding and moving the test subject 120. The working ends 123 and 124 are concave in the exemplary illustration of FIG. 4. Two further sliders 127 and 128 reside in the slot 115. These have larger ends 129 and 130 dimensioned to be guided in their movement by sides of the slot 115. The sliders 127 and 128 have slender probes 133 and 134 forming tiny working ends 138 and 139 secured to the test subject 120 by an appropriate glue. Two paddle-like force transmitting members 141 and 142 extend into slots 143 and 144 of the sliders 127 and 128.

For working with small specimens the base and slider arrangement of FIG. 4 enables the experimenter to position the test subject 120 at the intersection of the two guideway slots 115 and 116, using the two sliders 117 and 118, so that, the probe-like ends 138 and 139 of the two working sliders 127 and 128, each bearing a drop of glue, can be moved into contact with the test subject. The positioning sliders 117 and 118 can then be retracted and the forcing frame can be employed to apply force to the test subject 120.

In the alternate embodiment of FIG. 5, forces are applied to a test subject 150 along orthogonal axes. Sliders 158 to 161 received in perpendicular guideways 153 and 154 of a base 155 are like the sliders 127 and 128 described with reference to FIG. 4. Using sliders like the positioning sliders 117 and 118 of FIG. 4, the test subject 150 is positioned at the intersection of the two guideways 153 and 154. Two of the sliders 158 to 161 have their working ends brought into contact with the subject 150. Again a suitable glue can be applied. The positioning sliders can then be removed from the guideway and the remaining two of the sliders 158 to 161 can have their tips secured to the test subject 150. Force transmitting members 165 and 166 of a first forcing frame generally indicated at 171, in phantom outline, are introduced into slots in the sliders 158 and 160. The frame 171 is located above the base 155. The force transmitting members 168 and 169 of a second forcing frame, generally indicated at 172, in phantom outline, are introduced into slots in the sliders 159 and 161. The frame 172 is located to the side of the base 155 and its force transmitting members reach in from the side, not to interfere with the frame 171. The two forcing frames can be used to apply forces to the test subject 150 along the axes established by the guideways 153 and 154.

Figure 6:
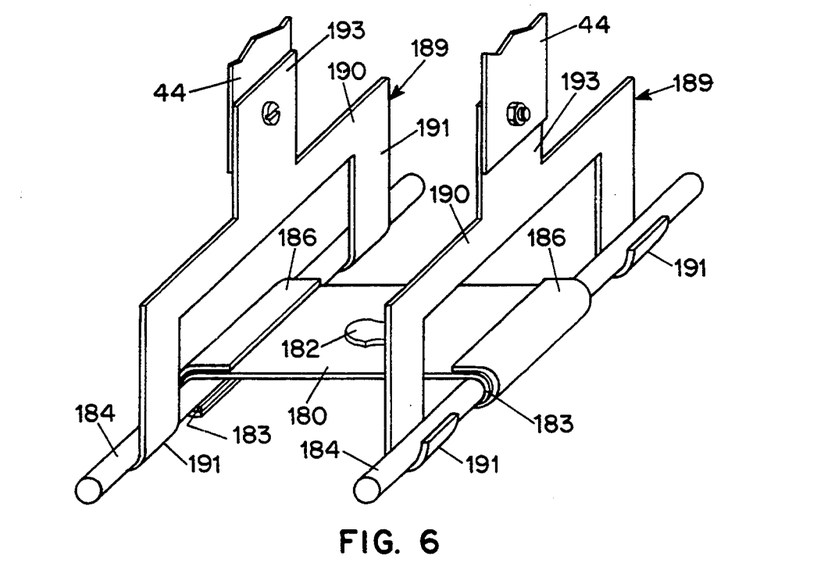
FIG. 6 is a partially fragmentary perspective view of a coupling apparatus for unidirectionally stretching a test subject affixed to an elastic support band.

Another configuration for applying force to a test subject is illustrated in FIG. 6. A rectangular elastic band 180 applies stretching forces along the length of a test subject 182. Two opposite ends 183 of the support band 180 wrap partially around a pair of stainless steel rods 184. Two semi-cylindrical retainers 186, made of resilient plastic, snap over the rods 184 to fit tightly in partially encircling relation, trapping the support band ends 183 between the rods and the retainers. Specially configured force transmitting members 189 have a horizontal bar 190 with curved fingers 191 on either end. The curved fingers 191 hold the rods 184 at locations on opposite sides of the band 180. A central stem 193 of each force transmitting member is secured by nuts and bolts to the shims 44 of a forcing frame like the frames previously described. The shims 44 are forced apart as desired, to cause stretching of the band 180. Stretching of the band 180 is nearly entirely unidirectional, so the test subject 182 is likewise subjected to a unidirectional stretching applied along the length of the subject.

Figure 7:
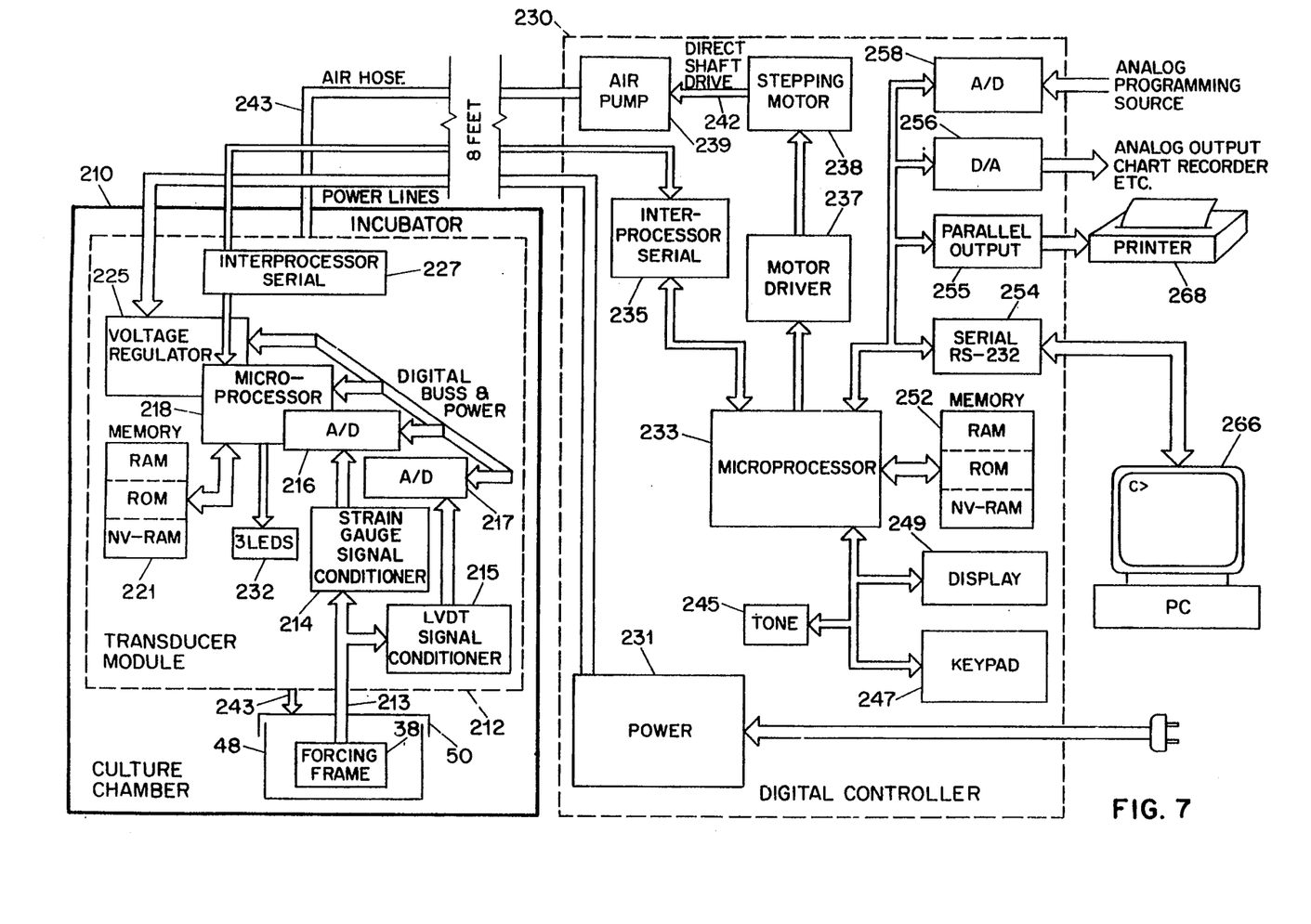
FIG. 7 is a schematic illustration in block diagram form of a controller and transducer module in association with the force generating device of FIG. 1.

In FIG. 7 controls suitable for controlling various force applications, applying dimensional constraints, and providing force and dimension measurements are illustrated. The test container 48, with its force frame supporting lid 50, is shown located in an incubator 210. A transducer module 212 communicates with the strain gauges 88 and 90 (shown in FIG. 2) and the LVDT 78 (shown in FIG. 2) as indicated at 213. A strain gauge signal conditioner 214 and an LVDT signal conditioner 215 supply a pair of analog to digital converters 216 and 217 that convert force and dimensional indications from the strain gauges and LVDT to digital words appropriate to be handled by a microprocessor 218 and its associated memory 221. The LVDT signal conditioner 215 is the commercially available Signetics circuit mentioned above. The strain gauge signal conditioner 214 can include the connections of the gauges into a bridge and supply connection from a voltage regulator 225 plus such conventional circuit features as may be necessary or desired to provide a accurate strain gauge bridge analog output signal. Three LEDs 232 indicate when the module is on, indicate with a blink when a reading is taken, and indicate a detected malfunction like a failure to connect the LVDT. The transducer module microprocessor 218 communicates with a digital controller 230 via a serial data link or RS-445 interprocessor 227. LED indicators 232 can be controlled by the microprocessor 218 as desired.

The digital controller 230 is located outside the incubator 210. It includes a power supply 231 conventionally providing DC from, for example, 110 volt AC. This power supply can provide a first stage of DC voltage regulation for the transducer module 212, to reduce the need to include heat-producing components in the sealed transducer module. A microprocessor 233 communicates via a serial interprocessor data link 235 and cables as required. The microprocessor 233 controls a motor driver circuit 237, typically a commercially available circuit associated with a commercial stepper motor 238 that operates an air (or fluid) pump 239 via a cog belt drive 242. The air pump can be as described in the above-referenced '683 patent, or if desired, and particularly for application of greater forces, hydraulics can be employed. The pump 239 and its associated hose 243 communicates with the bellows 42 of the force frame (as shown in FIG. 2).

Also included in the controller 230 and connected in operative relation to the microprocessor 233 are an audible tone generating device 245, a keypad 247, a display 249, requisite memory 252, an RS-232 interface 254, a parallel output port 255, a digital to analog converter 256, and an analog to digital converter 258. Shown in association with the controller 230 is a personal computer 266 and a printer 268. The keypad 247 permits the user to program the force and/or dimensional constraints desired according to preset programs or programs of the user's own devising. The display 249 communicates to the user, for example prompting or displaying menus or the directions or parameters being introduced via the keypad 247. The RS-232 link 254 communicates between the microprocessor 233 and the PC 266. The printer 268 is connected to the microprocessor 233 via the parallel output port 255. The digital to analog converter 256 enables the use of a chart recorder or other analog output device, and the analog to digital converter 258 enables programming an experiment based on an analog input.

The transducer module microprocessor 218 has three basic functions. First, it controls and coordinates the digital conversion of the analog signals from the strain gauges and LVDT. Second, it processes commands coming to it from the microprocessor 233 of the controller 230 via serial communications links 235 and 227. Third, it sends digital force and position readings back to the controller 230 as requested by the controller microprocessor 233 via the serial links 227 and 235.

Inputs effecting the manner of operation of the forcing frame can be supplied to the controller 230 from various sources. The keypad 247, which may include push buttons and desired selector switches on the front panel of the controller, allows the operator to select options presented on the display, such as preprogrammed force application routines, like the constant target force and constant target dimension routines described below, or selected force or size variations regimens, for example. An analog function generator defining a particular force or dimension wave form can communicate to the microprocessor via the digital analog converter 256 so that a user-designed force or dimension wave form can be applied to a specimen. Likewise a user-designed experiment can be communicated to the microprocessor 233 via the RS-232 serial connection 254. And inputs of force, and position readings fed back from the forcing frame via the transducer module 212 are input to the controller microprocessor 233 via the interprocessor data links 227 and 235.

The controller microprocessor 233 has control over various outputs. These include commands sent to the transducer module 212 to request force and position data. The microprocessor 233 outputs stepper motor direction and amount of turning commands via the motor drive circuit 237. These output commands adjust the distance between the load cell shims 44 under the control of the bellows 42 (FIG. 2). Outputs to the visual display 249 are under the control of the microprocessor 233 as are outputs to the audible tone generator 245 alerting the operator to chosen conditions. Of course, the microprocessor 233 controls outputs to the analog output device, such as a chart recorder connected to the digital to analog converter 256 and controls output to the printer 268 via the port 255. The printer 268 can generate listings of experiment parameters and can generate graphs of force or displacement over time or listings of force and displacement in numerical form. Finally, the microprocessor 233 can provide output to the PC 266 enabling the PC to store force and displacement data, for example on disk, or enabling the PC to undertake calculations as may be desired by the experimenter, using force and displacement results.

Conventional programming enables the microprocessor 233 of the controller 230 to coordinate the interaction between the human operator and the machine, utilizing the keypad display 249 and tone generator 245. The operator instructs the controller 230 how an experiment is to be executed by entering various set up parameters in the controller, when prompted by the display. A particular test routine retained in memory 252 can be chosen for execution.

The microprocessor 233 maintains the correct force level defined by a target value of force or dimension chosen by the user and retained in memory for purpose of continuing comparison. This function has the highest priority. The target value is compared to the actual level as sensed by the strain gauges or the LVDT.

If constant target force is desired in a force controlled operation, the force frame will change the distance between the two depending shims 44 such that the target force is applied. For example, if the force frame were applying an axial compressive load to growing bone tissue, the load cell shims 44 would move closer to each other squeezing the tissue until the target force were reached. Then if the bone tissue were to grow axially, more force would be applied to the sample tissue. The microprocessor 233 would note the increased force and move these load cell shims 44 further apart until the force dropped down to the target value. A complementary example would be if a fiber were being stretched between the shims 44. The shims would move away from each other stretching the fiber until the target force was reached. If, over time, the fiber stretched, the force pulling on the load cell shims 44 would be reduced. The microprocessor 233 would note this and move the load cell shims 44 farther apart until the force increased to the target force value. The dimensional change could be monitored as the force was being maintained at a constant value.

If a constant target dimension were used, then the force would be adjusted on the test sample to maintain a particular dimension (strain controlled operation). In the above bone example, the bone would be compressed until the target dimension was reached. If the bone grew axially, the microprocessor 233 would note this increase of dimension and apply more compressive force until the bone was compressed to the target dimension. In the fiber example, the fiber would be stretched until the target dimension was reached. If the fiber stretched and the dimension increased, the microprocessor 233 would note this and decrease the force level until the dimension returned to the target dimension. In both examples, the force changes could be monitored as the dimension was held constant.

In the above examples, the target values were held constant. However, the target values can be set from the keypad 249, the analog function generator or the external PC 266 to change over time to meet the experimenter's needs. The controller microprocessor 233 can then be directed to change the target value in a periodic manner using sine, triangle, or square wave forms as dictated by memory 252, for example. Minimum and maximum values, duration of period and duty cycle can be set up by the operator at the keyboard 247. Also, custom wave forms of any form can be set to the microprocessor 233 from the external computer or the analog function generator. Controls of the above-mentioned kind are commonly programmed in industrial controllers with feedback capability and are a relatively routine programming procedure. The microprocessor 233 can readily be made to send force and dimensional readings to the display 249, the PC 266, the printer 268, or the analog output as the user desires.

The transducer module microprocessor 218 and the controller microprocessor in this embodiment are both INTEL 8031s. The source code listings for both microprocessors have been appended.

While there have been described what are at present considered to be the preferred embodiments of this invention, it will be obvious to those skilled in the art that various changes and modifications may be made therein without departing from the spirit and scope of the invention, as set forth in the appended claims. For example, it will be apparent that in the guideway and slider arrangements, the applied forces to test subject working portions of the sliders can be altered as desired to accommodate various test subjects and to apply forces to broader and narrower locations or to compress or stretch a subject. In fact, the versatility of the foregoing apparatus for applying forces, measuring applied force and measuring dimensional characteristics is among the advantages of the invention.

We claim:

1. A transducer module for use for interconnecting a Separate digital microprocessor-based controller module and electrically controlled testing provisions used in testing biological and biocompatible test subjects with a forcing frame adapted to apply force to the test subject and measure displacement of forcing frame members corresponding to dimensional change of the test subject, the transducer module being adapted for cooperation with the controller module, which programs control of the operation of the forcing frame, the transducer module comprising:

circuit means for connection with the forcing frame for conditioning signals representative of test data measurements received from the forcing frame, means for electrically communicating with the digital controller module including a communications means for outputting to the controller module digital electrical representations of test data measured, and digital electronic processing means connected with the signal conditioning means and the communication means for controlling the outputting of the digital electronic representations, the transducer module being housed separately from the controller unit.

2. The transducer module according to claim 1 wherein the digital electronic processing means comprises a microprocessor and memory, the memory storing programs controlling the outputting of the test data representative signals.

3. The transducer module according to claim 2 wherein the digital electronic processing means is responsive to commands received at the transducer module from the digital controller module via the communications means to pass test data out of the transducer module via the communications means.

4. In a laboratory test instrument system for applying forces to biological and biocompatible test subjects, including a controller module having a stepper motor, pump, a microprocessor and memory for programming the application of forces to the test subjects, and a forcing frame connected to the pump and having fluid driven force exerting means, distance measuring means and force measuring means, the improvement comprising;

a transducer module separately housed and separately locatable from the controller module, the transducer module having a microprocessor and memory, means for receiving distance and force indicative information inputs from the distance measuring means and force measuring means of the forcing frame, means for communicating the distance and force indicative information input from the controller module in digital form, said microprocessor and memory controlling the outputting of the force and dimensional information to the controller.

5. The transducer module according to claim 4 wherein the means for receiving distance and force indicative information inputs includes an LVDT signal conditioner for receiving LVDT linear distance-related signals from the forcing frame and a strain gauge signal conditioner for receiving strain gage force-related signals from the forcing frame.

6. The transducer module according to claim 5, further comprising means for receiving DC power to power the transducer module and interprocessor means for receiving communications from the controller module microprocessor.

* * * * *

UNITED STATES PATENT AND TRADEMARK OFFICE
CERTIFICATE OF CORRECTION

PATENT NO. : 5,452,236
DATED : September 19, 1995
INVENTOR(S) : Phillip M. Lintilhac and Thompson B. Vesecky It is certified that error appears in the above-indentified patent and that said Letters Patent is hereby corrected as shown below:

Title page, 2nd col, 6th line, "3/1976" should read --3/1986--;

Title page, 2nd col, 5th line, "62000135" should read --62-002135--; and

Col. 11, line 44, "Separate" should read --separate--.

Signed and Sealed this

Ninth Day of January, 1996

Attest:

BRUCE LEHMAN

Attesting Officer          Commissioner of Patents and Trademarks